United States Patent
Sampara et al.

[11] Patent Number: 6,100,363
[45] Date of Patent: Aug. 8, 2000

[54] ENERGY ABSORBING ELASTOMERS

[75] Inventors: Agus Sampara, Ann Arbor; Cal Peeler, Canton, both of Mich.; Kerry Bowman, Mississauga; Richard Jewell, Erin, both of Canada

[73] Assignee: BASF Corporation, Mt. Olive, N.J.

[21] Appl. No.: 09/042,262

[22] Filed: Mar. 13, 1998

[51] Int. Cl.[7] .......................... C08G 18/48; C08G 18/65; C08G 18/32
[52] U.S. Cl. ..................... 528/76; 524/700; 524/705; 524/871; 524/791; 528/48; 528/74.5; 528/80; 528/85; 527/500
[58] Field of Search ....................... 524/700, 705, 524/871, 791; 528/48, 74.5, 76, 80, 85; 527/500

[56] References Cited

U.S. PATENT DOCUMENTS

| | | | |
|---|---|---|---|
| 3,959,573 | 5/1976 | Eddy et al. | 492/56 |
| 4,237,237 | 12/1980 | Jarre et al. | 521/128 |
| 4,279,757 | 7/1981 | DeBeuckelaer et al. | 210/671 |
| 4,661,532 | 4/1987 | Morin | 521/167 |
| 4,677,157 | 6/1987 | Jacobs | 524/789 |
| 5,405,885 | 4/1995 | Sampara et al. | 521/132 |
| 5,476,681 | 12/1995 | Sampara et al. | 427/140 |
| 5,688,860 | 11/1997 | Croft | 524/710 |

FOREIGN PATENT DOCUMENTS

95/20002  7/1995  WIPO .

OTHER PUBLICATIONS

Abstract of JP4008717; WPI Accession No. 92–061809(30).
Saunders et al.; Polyurethanes, Chemistry and Technology, Part I. Chemistry; Interscience Publishers; New York; 1962; pp. 264, 284, 293, 294, and 314.
Saunders et al.; Polyurethanes, Chemistry and Technology, Part II. Technology; Interscience Publishers, New York; 1964; pp. 308 and 340–342.

*Primary Examiner*—Rabon Sergent
*Attorney, Agent, or Firm*—Fernando A. Borrego

[57] ABSTRACT

The present invention relates to energy absorbing elastomers having a resilience of no more than 20.0% according to ASTM D2632-92. The energy absorbing elastomers are hydrophobic in nature and have extended gel times thus making them suitable for high volume applications such as coating a large substrate or filling a large void between two substrates.

19 Claims, 1 Drawing Sheet

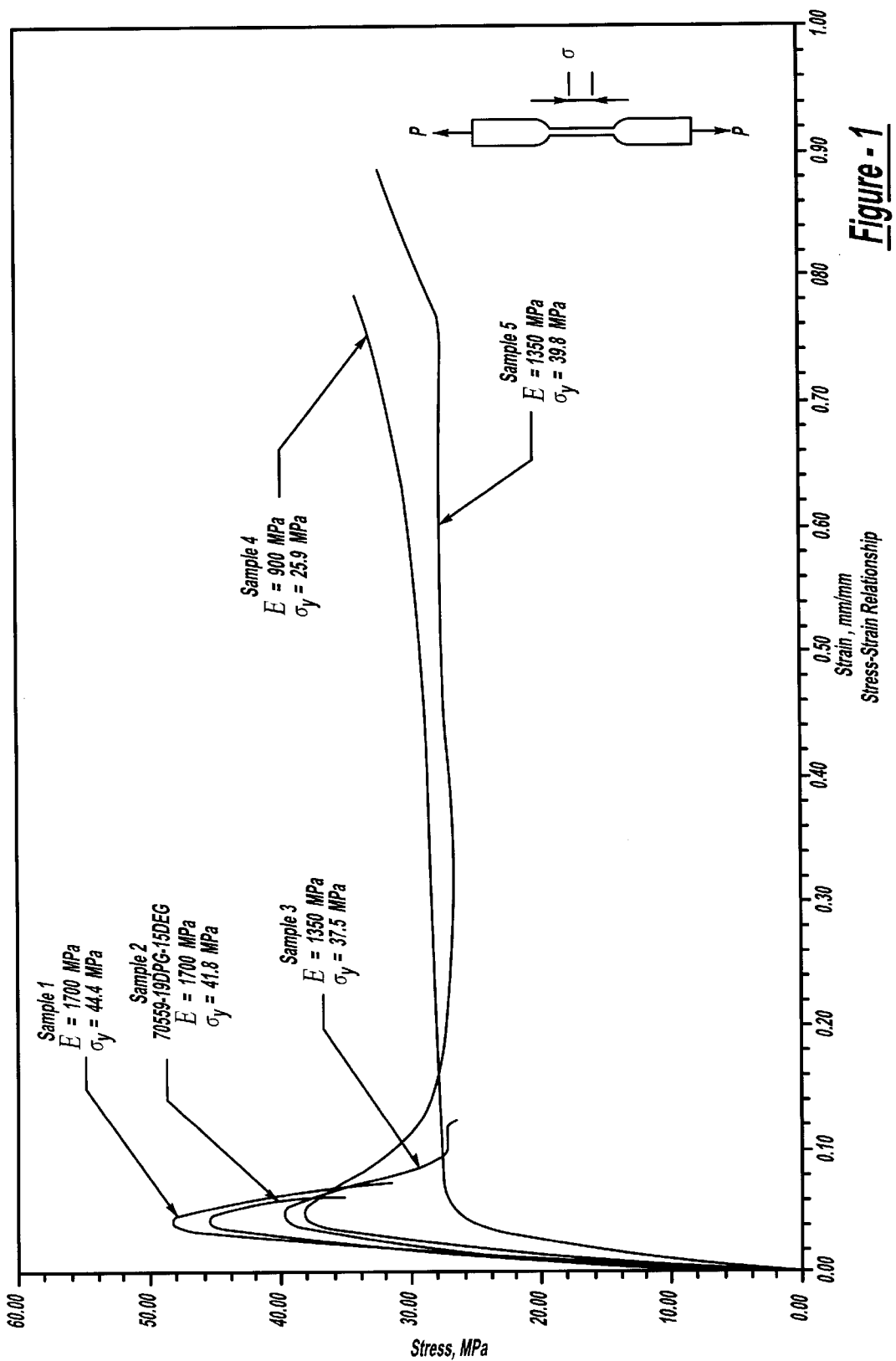

ENERGY ABSORBING ELASTOMERS

FIELD OF THE INVENTION

The present invention relates to energy absorbing elastomers, and more particularly, to polyurethane based energy absorbing elastomers useful for coating large objects filling a void between two substrates, and where moisture resistance is an important consideration.

BACKGROUND OF THE INVENTION

Elastomers per se have become increasingly useful for a wide range of commercial applications. For example, it is believed that certain elastomers are now being employed in the automobile industry as attachments to autobody panels as rust inhibitors or for sound attenuation. While the known elastomers are apparently useful for their intended purpose in association with relatively small objects such as autobody panels, larger objects pose unique considerations which must be addressed.

By way of a non-limiting example, in order to fill a large void between two substrates with an energy absorbing elastomer, the elastomer employed must have a relatively slow gel time in order to coat the entire surface prior to curing. Further, the energy absorbing elastomer may need to be relatively lightweight and hydrophobic particularly in environments where high levels of condensation normally occur. Preferably, the energy absorbing elastomer employed will have excellent adhesion, wear resistance ductility and will exhibit nominal shrinkage.

SUMMARY OF THE INVENTION

It is therefore an object of the present invention to provide an elastomeric composition which addresses each above described considerations. Thus, there is provided an elastomer comprising the reaction product of:

a) an organic polyisocyanate; and
b) a resinous material comprising:
   i) an active hydrogen containing composition including between about 10.0 wt. % and about 50.0 wt. % of a $C_{10}$ or higher hydrocarbon based on the total weight of b), a polyoxyalkylene polyol and a chain extender having a number average molecular weight of less than about 500;
   ii) a water scavenger; and
   iii) optionally, one or more compounds selected from the group consisting of cross-linkers, catalysts, antioxidants, UV-stabilizers, flame retardants, plasticizers, fillers, coloring agents and mixtures thereof;

The energy absorbing elastomers of the present invention can be utilized for a number of different applications including but not limited to filling a void between two substrates such as steel, particularly objects having double walled construction, which generally require a significant amount of time to coat and/or fill. While it is contemplated that the elastomeric compositions of the present invention are particularly useful for slow fill applications, i.e., those requiring an elastomer having a gel time of at least about 5 minutes, other applications requiring an energy absorbing elastomers are considered to be within the scope of the present invention.

The present invention also relates to the method of preparing energy absorbing elastomers and of coating objects or filling voids with the same.

DESCRIPTION OF THE DRAWING

FIG. 1 is a graph plotting the results of a stress-strain relationship for various samples following the method described by ASTM D412-83.

DETAILED DESCRIPTION OF A PREFERRED EMBODIMENT

The energy absorbing elastomers of the present invention can be utilized for a number of different applications including but not limited to coating large panels such or filling large voids. In general, it is contemplated that the energy absorbing elastomers of the present invention can be employed where moisture resistance is a particular concern due to the hydrophobic nature of the elastomer. As used herein, the phrase "energy absorbing elastomers" should be understood to include elastomers having a resilience of no more than 20.0% according to the method set forth under ASTM D2632-92.

To prepare the resinous material utilized in the elastomer an active hydrogen containing composition is employed which includes between about 10.0 to 50.0 wt. % of a $C_{10}$ or higher hydrocarbon based on the total of all resin components. More preferably, the active hydrogen containing composition will include between about 15.0 wt. % to about 45.0 wt. % of a $C_{10}$ or higher hydrocarbon and still more preferably between about 20.0 wt. % to about 35.0 wt. %.

Preferred examples of such compounds include polyols such as castor oil, castor-oil based or derived compounds, polybutadiene and saturated hydrocarbons. By $C_{10}$ or higher hydrocarbons, it is meant that the polyol employed will have a carbon chain length of ten or more as should be understood by those skilled in the art. By saturated hydrocarbons, it is meant that the polyols have no double bonds in their molecular structure.

Of the aforementioned, castor oils are considered to be particularly preferred. While numerous commercially available castor oil products are useful in accordance with the teachings of the present invention, one known as DB Oil which is available from CasChem, Inc., of Bayonne, N.J., has been found to be particularly useful. In this regard, it has been observed that castor oil not only appears to enhance the hydrophobicity of the polyurethane compositions, i.e. resistance to water absorption, for example, but also enhances the fire retardancy characteristics of the resulting product due to char formation caused by the relatively long hydrocarbon chain length.

Under certain applications, the active hydrogen containing composition will optionally include compounds which do not have at least two isocyanate-reactive hydrogens, such compounds being referred to herein as long chain hydrocarbons. Examples of such long chain hydrocarbons include, for example, and without intending to be limiting, paraffins, olefins, vegetable and animal oils and modifications of such materials. Particularly useful of the so-called long chain hydrocarbons are hydrocarbon oils and mono-functional long chain hydrocarbon compounds such as alcohol and/or fatty (long chain hydrocarbon) acids. In general, the longer the hydrocarbon chain length, the more hydrophobic in nature the hydrocarbon will be. The total amount of long chain hydrocarbons employed in the resin will range from about 5.0 to 30.0 weight % and more preferably from about 10.0 weight % to about 20.0 weight %.

In addition to the $C_{10}$ or higher hydrocarbon(s) employed, the hydrogen containing composition will include a certain amount of a polyoxyalkylene polyether polyol and at least one chain extender.

The polyoxyalkylene polyether polyols which are the polymerization product of an alkylene oxide with a polyhydric alcohol are those disclosed in U.S. Pat. No. 5,436,277, the disclosure of which is hereby expressly incorporated by reference. Any suitable alkylene oxide and mixtures thereof may be used such as ethylene oxide, propylene oxide, butylene oxide, amylene oxide, and mixtures of these oxides, preferably propylene oxide. Polyoxypropylene polyether polyols are more hydrophobic than their ethylene oxide counterparts. The polyalkylene polyether polyols may be prepared from other starting materials such as tetrahydrofuran and alkylene oxide-tetrahydrofuran mixtures; epihalohydrins such as epichlorohydrin; as well as aralkylene oxides such as styrene oxide. The polyalkylene polyether polyols may have either primary or secondary hydroxyl groups. Included among the polyether polyols are polyoxyethylene glycol, polyoxypropylene glycol, polyoxybutylene glycol, polytetramethylene glycol, block copolymers, for example, combinations of polyoxypropylene and polyoxyethylene glycols, poly-1,2-oxybutylene and polyoxyethylene glycols, poly-1,4 tetramethylene and polyoxyethylene glycols, and copolymer glycols prepared from blends or addition of two or more alkylene oxides. The polyalkylene polyether polyols may be prepared by any known process such as, for example, the process disclosed in the *Encyclopedia of Chemical Technology*, Vol. 7, pp. 257–262, published by Interscience Publishers, Inc. (1951) or in U.S. Pat. No. 1,922,459; all of which are expressly incorporated herein by reference.

While polyester polyols are generally less preferred than polyether polyols in that they tend to be less soluble than polyether polyols, a limited amount of polyester polyols may be employed along with the polyester polyols. Suitable hydroxy-terminated polyesters include those obtained, for example, from polycarboxylic acids and polyhydric alcohols. A suitable polycarboxylic acid may be used such as oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, a-hydromuconic acid, B-hydromuconic acid, a-butyl-a-ethyl-glutaric acid, a,B-diethylsuccinic acid, isophthalic acid, therephthalic acid, phthalic acid, hemimellitic acid, and 1,4-cyclohexanedicarboxylic acid. Suitable polyhydric alcohol include, in a non-limiting manner, ethylene glycol, propylene glycol, trimethylene glycol, neopentyl glycol, 1,2-butanediol, 1,4-butanediol, 1,5-pentanediol, 1,6-hexanediol, 1,7-heptanediol, 2-methyl-1,3-propanediol, hydroquinone, resorcinol glycerol, glycerine, 1,1,1-trimethyiol-propane, 1,1,1-trimethylolethane, 1,2,6-hexanetriol, a-methyl glucoside, sucrose, and sorbitol. Again, mixtures of such alcohols may be employed. Also included within the term "polyhydric alcohol" as used herein are compounds derived from phenol such as 2,2-bis(4-hydroxyphenyl)-propane, commonly known as Bisphenol A. The polyester polyols, if employed, will preferably have molecular weights from 500 to 10,000, more preferably from 750 to 8000, and still more preferably from 1000 to 6000.

The amount of polyoxyalkylene polyether polyols employed in the energy absorbing elastomers of the present invention will generally range from about 10.0 wt. % to about 60.0 wt. %, more preferably from about 15.0 wt. % to about 55.0 wt. %, and still more preferably from about 20.0 wt. % to about 50.0 wt. % based on the total of all components.

Of the above listed polyhydric alcohols, those having number average molecular weights of less than about 500, more preferably from 50 to 400 and still more preferably from 60 to 300 may be employed as chain extenders in accordance with the teachings of the present invention. As such, 1,4 butanediol, diethyleneglycol, dipropylene glycol, 1,5 pentanediol, neopentyl glycol, hexanediol and mixtures thereof are considered to be the preferred chain extenders. Preferably the total amount of chain extender employed in the energy absorbing elastomers of the present invention will be a positive amount of up to 30.0 wt. % based on the total of all resin components. More preferably, the total amount of chain extender to be employed will be between about 2.0 wt. % to about 20.0 wt. % and still more preferably between about 5.0 wt. % to about 10.0 wt. %. By the phrase "a positive amount" it is meant that greater than 0.0 wt. % of a chain extender will be employed.

Water scavengers will be employed in an effort to prevent water contained in the composition from reacting with the isocyanates which in turn prevents the formation of $CO_2$ and thus limits or precludes foaming. Molecular sieves which are generally silica based have proven useful as water scavengers in elastomeric systems. Additionally, ZOLIDINE, which is a liquid oxazolidine available from Angus Chemicals, Inc. of Buffalo Grove, Ill., is contemplated as being useful. In general, the total amount of water scavengers necessary to limit and preferably preclude foaming of the elastomer ranges from about 0.05 weight % to 5.0 weight % and more preferably from 1.0 weight % to about 3.0 weight %.

In addition to the water scavengers employed, one or more conventional additive components at conventional levels selected from the group consisting of cross-linkers, catalysts, anti-oxidants, UV-stabilizers, flame retardants, fillers, coloring agents and mixtures thereof may be incorporated in the elastomer of the present invention. Suitable examples of cross-linkers useful in accordance with the practice of the present invention include, without limitation, the alkylene oxide addition products of trimethylolpropane, glycerine, sucrose, sorbitol, propylene glycol, dipropylene glycol, pentaerythritol, and 2,2-bis (4-hydroxyphenyl)-propane and blends thereof having equivalent weights of from about 31–340.

Catalysts may also be employed in accordance with the teachings of the present invention. The catalyst generally accelerate the reaction of the active hydrogen containing compounds with the organic polyisocyanates. Examples of useful catalysts include organic metal compounds, preferably organic tin compounds such as tin (II) salts of organic carboxylic acids, e.g., tin(II) acetate, tin(II) octoate, tin(II) ethylhexoate and tin(II) laurate, as well as the dialkyline(IV) salts of organic carboxylic acids, e.g., dibutyltin diacetate, dibutyltin maleate and dioctylin diacetate. Specific examples of organic tin compounds which are useful include, without limitation, dibutyltin dilaureate, dibutyltin sulfide and tin mercaptans, among others. Other organic metal compounds which are considered useful include zinc compounds such as zinc octoate with bismuth compounds. Organometallic compounds useful as catalysts are generally disclosed in U.S. Pat. No. 2,846,408, the disclosure of which is incorporated herein by reference. The organic metal compounds are used alone or preferably in combination with strong basic amines.

Examples include amidines such as 2,3-dimethyl-3,4,5,6-tetrahydropyrimidine, tertiary amines such as triethylamine, tributylamine, dimethylbenzylamine, N-methylmorpholine, N-ethylmorpholine, N-cyclohexylmorpholine, N,N,N',N'-tetramethylethylenediamine, N,N,N',N'-tetramethylbutanediamine, pentamethyldiethylentriamine, tetramethyldiaminoethyl ester bis(dimethylaminopropyl) urea, dimethylpiperazine, 1,2-dimethylimidazle, 1-azabicyclo[3.3.0]octane and preferably 1,4-diazabicyclo[2.2.2] octane, 1,8 diazabicyclo 5,4,0 undecene 7 and alkanolamine compounds such as triethanolamine, triisopropanolamine, N-methyl-and N-ethyldiethanolamine and dimethylethanolamine.

Suitable catalysts also include tris(dialkylamino)-s-hexahydrotriazines, especially tris(N,N-dimethylaminopropyl)-s-hexahydrotriazine, tetraalkylammonium hydroxides such as tetramethylammonium dydroxide, alkali hydroxides such as sodium hydroxide and alkali alcoholates such as sodium methylate and potassium isopropylate as well as alkali salts of long-chain fatty acids with 10 to 20 carbons and optionally OH side groups. An effective amount of catalyst to promote the reaction of isocyanate groups with the polyol, or with other isocyanate groups in the case of isocyanurates, is to be employed.

Anti-oxidants may also be employed if necessary to retard the oxidation of the reacted urethane. Preferred among the numerous commercially available anti-oxidants which are considered useful are: Irganox, available from Ciba-Geigy Corp., of Greensboro, N.C.; and Cyanox, available from Cytec, Industries Inc., of Havre De Grace, Md.; both are particularly useful. Mixtures of anti-oxidants may also be employed.

UV stabilizers which can be employed include, without limitation, benzophenones, benzotriazoles, substituted acrylonitriles, phenol-nickel complexes, and mixtures thereof. Examples of commercially available UV-stabilizers include Tinuvin, available from Ciba-Geigy Corp., of Greensboro, N.C., and Uvinul, available from BASF Corporation of Mt. Olive, N.J.

It may be desirable in certain applications to employ one or more flame-retardants. For example, certain flame retardants which are reactive with isocyanates which may be employed include phosphor-based products such as Fyrol 6 and Fyrol 51, available from Akzo Chemicals, Inc., of Chicago, Ill.; and Vircol 82 available from Mobil Chemical Co., of Norwalk, Conn. Additionally, certain halogen based flame retardants, such as FR-522 and Saytex FR-1138 (which are dibromopentyl glycol based products available from AmeriBrom, Inc., and Ethyl Corporation of Richmond, Va., respectively), may be employed. Still other flame retardants which are generally non-reactive to the isocyanates may be employed.

Other conventional additives including, but not limited to, plasticizers, reactive and non-reactive silicone oils, fillers and coloring agents including dyes and pigments may also be employed, at conventional or art-disclosed levels. Included in the class of additive materials generally referred to herein as fillers are fibrous and particulate materials, non-polar polymeric materials and inorganic anti-block agents. Examples of such materials include glass and carbon fibers, silicas, calcium carbonate, clay, mica, talc, carbon black, particulate graphite and metallic flakes, among others.

To gain a further understanding of the various optional components which can be employed, reference can be made to various technical publications including, for example, the article by J. H. Saunders and K. C. Frisch, High Polymers, Volume XVI, Polyurethane, Parts 1 and 2 (Interscience Publishers 1962 and 1964), Kunstostoff-Handbuch, Volume 7, Polyurethane 1st and 2nd Editions (Carl Hanser Verlag, 1966 and 1994) or DE-A 29 01 774, which are hereby expressly incorporated by reference.

As previously alluded to, the resinous material is blended with certain isocyanate compounds in order to obtain the energy absorbing elastomer. Among the numerous isocyanates, otherwise referred to herein as organic isocyanates, which are considered useful are those including aromatic, aliphatic, and cycloaliphatic polyisocyanates and combinations thereof. Examples of such isocyanates may found at columns 8 and 9 of U.S. Pat. No. 4,690,956, herein incorporated by reference. Representative polyisocyanates are the diisocyanates such as m-phenylene diisocyanate, 2,4-toluene diisocyanate, 2,6-toluene diisocyanate, mixtures of 2,4- and 2,6-toluene diisocyanate, hexamethylene diisocyanate, tetramethylene diisocyanate, cyclohexane-1,4 diisocyanate, hexahydrotoluene diisocyanate (and isomers), naphthalene-1,5-diisocyanate, 1-methoxyphenyl-2,4-diisocyanate, 4,4'-diphenylmethane diisocyanate, 4,4'-biphenylene diisocyanate, 3,3'-dimethoxy-4,4'-biphenyl diisocyanate, 3,3'-diimethyl-4,4'-biphenyl diisocyanate and 3,3'-dimethyldiphenylmethane-4,4'-diisocyanate; the triisocyanates such as 4,4',4"-triphenylmethane triisocyanate, and toluene 2,4,6-triisocyanate; and the tetraisocyanates such as 4,4'-dimethyldiphenylmethane-2,2'-5,5'-tetraisocyanate and polymeric polyisocyanates such as polymethylene polyphenylene polyisocyanate, and mixtures thereof.

For preparation of the energy absorbing elastomers of the present invention, the ratio of the equivalent weight of the isocyanate component (a) to the resin component (b) is from 1.1:1.0 to 0.9:1.0, with a preferred ration being 1.0:1.0.

Suitable methods of preparing the energy absorbing elastomers of the present invention, particularly for purposes of property analysis, include adding the $C_{10}$ or higher hydrocarbon polyoxyalkylene polyol and chain extender with mixing to a vessel. If necessary, the vessel can be heated to approximately 140° F. to assist in obtaining a homogenous mixture. Thereafter, each of the other optional components including one or more compounds selected from the group consisting of cross-linkers, catalysts, anti-oxidants, UV-stabilizers, flame retardants, plasticizers, fillers, coloring agents and mixtures thereof, excepting any water scavengers are charged to the mixing vessel and blended. Upon blending, the water level of the composition is typically measured to determine whether the water level is below approximately 0.03 wt. % based on the total weight of the composition. If the water is above that level, the composition is heated further under vacuum to drive off water; however, if the water level is at or below this level, a water scavenger is added to the mixture with blending. Upon thoroughly blending the components, a resinous material results. Thereafter, the resin is blended with the organic isocyanate to form the energy absorbing elastomer of the present invention as set forth by way of non-limiting example below.

TABLE 1

| Sample | 1 | 2 | 3 | 4 | 5 |
|---|---|---|---|---|---|
| Castor Oil | 64.5 | 65.5 |  | 74.5 | 20.0 |
| Dipropyleneglycol | 22.0 | 19.0 |  |  |  |
| Diethyleneglycol | 8.0 | 15.0 |  |  |  |
| 1,4 Butanediol | 5.0 |  | 30.0 | 25.0 | 28.5 |
| Water scavenger[1] | 0.5 | 0.5 | 0.5 | 0.5 | 0.5 |
| Polyol A[2] |  |  | 69.5 |  | 51.0 |
| Iso A[3] | 104.0 | 102.0 | 104.0 | 103.0 | 103.0 |

[1]The water scavenger employed is a silica powder molecular sieve having a 3A commercial designation and is available from UOP.
[2]Polyol A is a diol-initiated propylene oxide/ethylene oxide copolymer having a hydroxyl number of 90 and a functionality of 1.98.
[3]is a polymeric MDI.

Upon preparing Samples 1–5 set forth in Table 1 above, the stress-strain relationship of each sample in accordance with the procedures outlined in ASTM D412-83 was measured and recorded as shown in FIG. 1. The objective of the analysis was to determine which elastomer compositions were capable of withstanding an exerted stress of at least 30 MPa and an exerted strain of greater than 20%.

As demonstrated in FIG. 1, Samples 1–3 had good stress capabilities but strained too easily. Sample 4 had less favorable stress capabilities but improved strain over Samples 1–3. Of the compositions tested in accordance with ASTM D412-83, only Sample 5 met both the stress and strain objectives.

While it will be apparent that the preferred embodiments of the invention disclosed are well calculated to fulfill the objects stated, it will be appreciated that the invention is susceptible to modification, variation and change without departing from the spirit thereof.

What is claimed is:

1. An elastomer comprising:
the reaction product of:
 a) an organic polyisocyanate; and
 b) a resinous material comprising:
  i) an active hydrogen containing composition including between about 10.0 weight % and about 50.0 weight % of a $C_{10}$ or higher hydrocarbon based on the total weight of b), said $C_{10}$ or higher hydrocarbon having at least two isocyanate reactive hydrogens, a polyoxyalkylene polyol and a chain extender having a number average molecular weight of 500 or less, said chain extender being other than said $C_{10}$ or higher hydrocarbon and said polyoxyalkylene polyol;
  ii) a water scavenger, present in an amount of from about 0.05 weight percent to about 5.0 weight percent based on the total weight of b); and
  iii) optionally, one or more compounds selected from the group consisting of cross-linkers, catalysts, anti-oxidants, UV-stabilizers, flame retardants, plasticizers, fillers, coloring agents and mixtures thereof; and
 wherein said elastomer has a resilience of no more than 20.0% according to ASTM D2632-92 and a gel time of greater than five minutes.

2. The elastomer of claim 1 wherein said $C_{10}$ or higher hydrocarbon is present in an amount of between about 20.0 weight % to about 35.0 weight % based on the total weight of b).

3. The elastomer of claim 1 wherein said $C_{10}$ or higher hydrocarbon is castor oil.

4. The elastomer of claim 1 wherein said polyoxyalkylene polyol is present in an amount of between about 10.0 weight % and about 60.0 weight % based on the total weight of b).

5. The elastomer of claim 1 wherein said polyoxyalkylene polyol is present in an amount of between about 20.0 weight % and about 50.0 weight % based on the total weight of b).

6. The elastomer of claim 1 wherein said polyoxyalkylene polyol is a diol-initiated propylene oxide/ethylene oxide copolymer.

7. The elastomer of claim 1 wherein said chain extender is present in a positive amount up to about 35.0 weight % based on the total weight of b).

8. The elastomer of claim 1 wherein said chain extender is present in an amount of between about 5.0 weight % and about 10.0 weight % based on the total weight of b).

9. The elastomer of claim 8, wherein said chain extender is selected from the group consisting of 1,4 butanediol, diethyleneglycol, dipropylene glycol, 1,5 pentanediol, neopentyl glycol, hexanediol and mixtures thereof.

10. A method of making an elastomer comprising the steps of:
 a) providing an organic polyisocyanate;
 b) providing a resin comprising:
  i) an active hydrogen containing composition including between about 10.0 weight % and about 50.0 weight % of a $C_{10}$ or higher hydrocarbon based on the total weight of b), said $C_{10}$ or higher hydrocarbon having at least two isocyanate reactive hydrogens, a polyoxyalkylene polyol and a chain extender having a number average molecular weight of 500 or less, said chain extender being other than said $C_{10}$ or higher hydrocarbon and said polyoxyalkylene polyol;
  ii) a water scavenger, present in an amount of from about 0.05 weight percent to about 5.0 weight percent based on the total weight of b); and
  iii) optionally, one or more compounds selected from the group consisting of cross-linkers, catalysts, anti-oxidants, UV-stabilizers, flame retardants, plasticizers, fillers, coloring agents and mixtures thereof;
 c) introducing a) and b) together while blending the same to produce an elastomer, said elastomer having a resilience of no more than 20.0% according to ASTM D2632-92 and a gel time of greater than five minutes.

11. The elastomer of claim 10 wherein said $C_{10}$ or higher hydrocarbon is present in an amount of between about 20.0 weight % to about 35.0 weight % based on the total weight of b).

12. The method of claim 10 wherein said $C_{10}$ or higher hydrocarbon is castor oil.

13. The method of claim 10 wherein said polyoxyalkylene polyol is present in an amount of between about 10.0 weight % and about 60.0 weight % based on the total weight of b).

14. The method of claim 10 wherein said polyoxyalkylene polyol is present in an amount of between about 20.0 weight % and about 50.0 weight % based on the total weight of b).

15. The method of claim 10 wherein said polyoxyalkylene polyol is a propylene diol-initiated oxide/ethylene oxide copolymer.

16. The method of claim 10 wherein said chain extender is present in a positive amount of up to about 35.0 weight % based on the total weight of b).

17. The method of claim 10 wherein said chain extender is present in an amount of between about 5.0 weight % and about 10.0 weight % based on the total weight of b).

18. The method of claim 10 wherein said chain extender is selected from the group consisting of 1,4 butanediol, diethyleneglycol, dipropylene glycol, 1,5 pentanediol, neopentyl glycol, hexanediol and mixtures thereof.

19. An elastomeric article having a resilience of no more than 20.0% according to ASTM D2632-92 comprising:
the reaction product of
 a) an organic polyisocyanate; and
 b) a resinous material comprising:
  i) an active hydrogen containing composition including between about 10.0 weight % and about 50.0 weight % of a $C_{10}$ or higher hydrocarbon based on the total weight of b), said $C_{10}$ or higher hydrocarbon having at least two isocyanate reactive hydrogens, a polyoxyalkylene polyol and a chain extender having a number average molecular weight of 500 or less, said chain extender being other than said $C_{10}$ or higher hydrocarbon and said polyoxyalkylene polyol;
  ii) a water scavenger, present in an amount of from about 0.05 weight percent to about 5.0 weight percent based on the total weight of b); and
  iii) optionally, one or more compounds selected from the group consisting of cross-linkers, catalysts, anti-oxidants, UV-stabilizers, flame retardants, plasticizers, fillers, coloring agents and mixtures thereof; and
wherein said elastomeric article has a gel time of greater than five minutes.

* * * * *